United States Patent
Leyer et al.

(10) Patent No.: US 9,410,918 B2
(45) Date of Patent: Aug. 9, 2016

(54) WATER ANALYSIS SENSOR ELECTRODE

(75) Inventors: Axel Leyer, Moenchengladbach (DE); Lothar Heidemanns, Korschenbroich (DE); Andreas Jonak, Meerbusch (DE); Markus Hahn, Kempen (DE); Michael Kussmann, Duesseldorf (DE); Andreas Golitz, Moers (DE); Aurelia Stellmach-Hanulok, Wuelfrath (DE); Claudia Rieger, Duesseldorf (DE); Heinz Rudde, Hueckelhoven (DE)

(73) Assignee: HACH LANGE GMBH, Berlin (DE)

( * ) Notice: Subject to any disclaimer, the term of this patent is extended or adjusted under 35 U.S.C. 154(b) by 729 days.

(21) Appl. No.: 13/809,894

(22) PCT Filed: Jul. 13, 2011

(86) PCT No.: PCT/EP2011/061928
§ 371 (c)(1),
(2), (4) Date: Mar. 20, 2013

(87) PCT Pub. No.: WO2012/007492
PCT Pub. Date: Jan. 19, 2012

(65) Prior Publication Data
US 2013/0168245 A1 Jul. 4, 2013

(30) Foreign Application Priority Data
Jul. 15, 2010 (EP) .................................. 10169615

(51) Int. Cl.
*G01N 27/333* (2006.01)
*G01N 27/28* (2006.01)
*G01N 33/18* (2006.01)

(52) U.S. Cl.
CPC .............. *G01N 27/333* (2013.01); *G01N 27/28* (2013.01); *G01N 33/18* (2013.01)

(58) Field of Classification Search
None
See application file for complete search history.

(56) References Cited

U.S. PATENT DOCUMENTS 4,838,999 A 6/1989 Haar et al.
2011/0308946 A1 12/2011 Wilke

FOREIGN PATENT DOCUMENTS

DE 89 12 731 U1 2/1990
DE 297 09 141 U1 8/1997
DE 10 2008 055084 A1 6/2010

OTHER PUBLICATIONS

Deveau et al. (Biol. Proced. Online 2005; 7(1): 31-40).*

* cited by examiner

*Primary Examiner* — Luan Van
*Assistant Examiner* — Steven Rosenwald
(74) *Attorney, Agent, or Firm* — Norman B. Thot

(57) ABSTRACT

A water analysis sensor electrode for determining an analyte in water includes a sensor electrode housing which is configured to be closed. The sensor electrode housing comprises an inner wall and an ion-selective sensor electrode diaphragm arranged at a lower distal end of the sensor electrode housing. An electrolyte solution is in the sensor electrode housing. A measuring electrode is arranged in the sensor electrode housing. A gas bubble is enclosed by the sensor electrode housing. A rigid rod element having a round cross section is arranged in the sensor electrode housing so that a continuous open capillary channel extends over a length of the sensor electrode housing between the rigid rod element and the inner wall.

11 Claims, 1 Drawing Sheet

WATER ANALYSIS SENSOR ELECTRODE

CROSS REFERENCE TO PRIOR APPLICATIONS

This application is a U.S. National Phase application under 35 U.S.C. §371 of International Application No. PCT/EP2011/061928, filed on Jul. 13, 2011 and which claims benefit to European Patent Application No. 10169615.1, filed on Jul. 15, 2010. The International Application was published in German on Jan. 19, 2012 as WO 2012/007492 A1 under PCT Article 21(2).

FIELD

The present invention relates to a water analysis sensor electrode for determining an analyte in water.

BACKGROUND

The sensor electrode comprises a closed sensor electrode housing with an electrolyte solution, for example, a pH buffer solution, a measuring electrode arranged in the electrolyte solution, and a gas bubble enclosed in the sensor electrode housing. The lower distal end of the sensor electrode housing is closed with an ion-selective sensor electrode diaphragm. The gas bubble is necessary to compensate for the temperature dependent volume change of the buffer solution.

Such sensor electrodes are described, for example, in DE 10 2008 055 084 A1 where the sensor electrode has an inner diameter smaller than 15.0 mm. When a sensor electrode of such a narrow diameter is turned upside down during transport, for instance, the gas bubble enclosed in the sensor electrode housing moves against the effect of gravity into the region between the sensor electrode diaphragm and the measuring electrode where it settles. When the sensor electrode is turned by 180° for assembly, the gas bubble remains in this region due to the phenomenon of surface tension. This trapping of the gas bubble has the effect that the electric connection between the sensor electrode diaphragm and the measuring electrode is interrupted. The problem of the gas bubble being trapped is conventionally overcome by carefully striking against the sensor electrode until the gas bubble is released and rises upward against the effect of gravity. No optical control is generally possible since the interior of the housing is not visible.

A sensor electrode is described in U.S. Pat. No. 4,838,999 wherein, in an attempt at reducing Ohmic resistance between two liquid volumes separated by a gas bubble, it is proposed providing a thread that soaks up electrolyte solution so that the electric resistance between the two liquid volumes is thereby drastically reduced. As an alternative, it is proposed providing a capillary channel that is integrated in the housing wall in the longitudinal direction of the housing and extending in the longitudinal direction. The manufacture of such a sensor electrode housing form is complex. The thread soaked with electrolyte solution may bridge the gas bubble, but cannot cause a flow of liquid under the gas bubble.

SUMMARY

An aspect of the present invention is to provide a water analysis sensor electrode wherein a trapping of the gas bubble within a liquid-filled sensor electrode housing is effectively avoided using simple means.

In an embodiment, the present invention provides a water analysis sensor electrode for determining an analyte in water includes a sensor electrode housing which is configured to be closed. The sensor electrode housing comprises an inner wall and an ion-selective sensor electrode diaphragm arranged at a lower distal end of the sensor electrode housing. An electrolyte solution is in the sensor electrode housing. A measuring electrode is arranged in the sensor electrode housing. A gas bubble is enclosed by the sensor electrode housing. A rigid rod element having a round cross section is arranged in the sensor electrode housing so that a continuous open capillary channel extends over a length of the sensor electrode housing between the rigid rod element and the inner wall.

BRIEF DESCRIPTION OF THE DRAWINGS

The present invention is described in greater detail below on the basis of embodiments and of the drawings in which.

DETAILED DESCRIPTION

Figure 1:
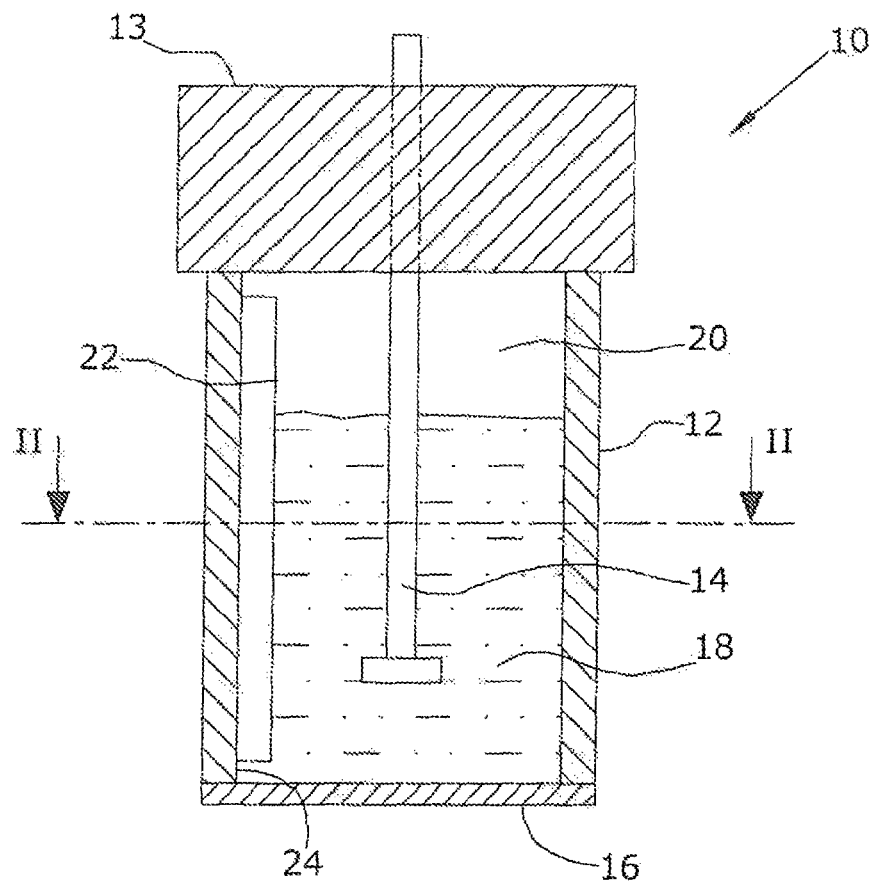
FIG. 1 shows a longitudinal section through the sensor electrode of the present invention.

The water analysis sensor electrode has a continuous open capillary channel inside the sensor electrode housing, which channel extends along the inner wall over the axial length of the sensor electrode housing. In the region of the capillary channel, the surface tension effect is weakened such that gravity is generally sufficient to make the electrolyte solution flow beneath a gas bubble situated at the bottom. When a gas bubble is present in the bottom portion of the sensor electrode, i.e., in the region between the sensor electrode diaphragm and the measuring electrode, electrolyte solution present in the sensor electrode housing flows under the gas bubble due to the capillary effect in the capillary channel. The electrolyte solution thus flows downward through the capillary channel to below the gas bubble and forces the gas bubble to rise against the effect of gravity so that the gas bubble moves upward from the above-mentioned region.

A chemically inert rod element of round, for example, circular cross section is placed into the, for example, circular sensor electrode housing, the rod element abutting on the inner wall of the housing. Due to the rod element abutting on the inner wall of the sensor electrode housing, a respective capillary channel is formed on either side of the rod element, the channel extending over the axial length of the rod element abutting on the inner wall. This rod element can be fixed on the inner wall using, for example, a tensioning clamp. A wall element can further be provided inside the sensor electrode housing, for example, on the lower face of the closing lid, which wall element limits the tilting movement of the rod element such that the rod element is secured against tilting. The rod element may alternatively be formed integrally with the sensor electrode housing so that, depending on the shape of the rod element, either one or two capillary channels are formed.

In an embodiment of the present invention, the rod element can, for example, abut inside the sensor electrode housing exclusively by adhesion to the inner wall and is not separately fixed mechanically. The rod element does not, however, have to be fixed permanently on the inner wall. It may temporarily become detached from this inner wall by shaking, for instance, but automatically returns to the inner wall due to the adhesion forces prevailing.

Due to the rod element being chemically inert, no chemical interaction with the electrolyte solution occurs so that the measuring quality of the sensor electrode is maintained. Possible materials from which the rod element can be made are glass, metal, ceramics or plastic materials. The density of the material used for the rod element should be higher than the density of the electrolyte solution so that the rod element rests on the bottom of the sensor electrode housing and the electrolyte solution can thus effectively flow to beneath the gas bubble.

In an embodiment of the present invention, the ratio of the diameters of the substantially-round rod element to the substantially-round sensor electrode housing can, for example, be less than 20. This provides that the capillary channel formed between the rod element and the inner wall has a sufficiently small wedge angle and thus the necessary capillary effect.

In an embodiment of the present invention, the axial length of the rod element can, for example, be at least 3.0 mm. It can, for example, be 5.0 mm larger than the height or the level of the electrolyte solution in the sensor electrode housing. In an embodiment of the present invention, the axial length of the rod element can, for example, be at least 3%, for example, 5% greater than the height or the level of the electrolyte solution in the sensor electrode housing. It is thereby provided that the rod element still extends into the gas bubble when it is in a diagonal position so that the active adhesion forces are sufficient to pull the rod element to the inner wall. In order to assist this movement, the bottom region of the sensor electrode housing can be provided with a positioning cone that always pushes the lower end of the rod element outward to the inner wall due to the effect of gravity.

In an embodiment of the present invention, the axial length of the rod element may be at least $7/10$ and at most $98/100$ of the axial inner length of the sensor electrode housing. The rod element is arranged inside the sensor electrode housing such that at least a part of the rod element always extends into the gas bubble. It is thereby provided that the gas bubble can always be flown under.

In an embodiment of the present invention, the sensor electrode housing can, for example, have an inner diameter of less than 15.0 mm. The smaller the inner diameter of the sensor electrode housing is, the stronger is the effect of the gas bubble being trapped, given a constant gas bubble volume. A capillary channel is therefore dispensable for larger inner diameters.

In an embodiment of the present invention, the capillary channel walls can, for example, include a wedge angle that is smaller than the contact angle defined by the housing material, the electrolyte solution and the gas. The contact angle is the angle a drop of a certain liquid forms on a planar surface of a certain material with respect to this surface.

An embodiment of the sensor electrode of the present invention will be explained in detail hereunder with reference to the drawings.

FIG. 1 illustrates a water analysis sensor electrode 10 for determining an analyte in water. The water analysis sensor electrode 10 is formed by a closed circular sensor electrode housing 12 with an inner diameter of about 6.0 mm, a measuring electrode 14 in the form of an Ag/AgCl wire positioned within the sensor electrode housing 12 on the axial line of the housing, and an ion-selective sensor electrode diaphragm 16 arranged at the lower, distal end. At the opposite end of the sensor electrode diaphragm 16, the sensor electrode housing 12 is sealed in a gas-tight manner by means of a closing lid 13.

The sensor electrode housing 12 is filled with an electrolyte solution 18 and further comprises an enclosed gas bubble 20, for example, an air bubble. Inserted into the sensor electrode housing 12 is a rod element 22, for example, a glass rod with a diameter of 1.0 mm, which abuts on an inner wall 24 of the sensor electrode housing 12 by adhesion. A part of the rod element 22 extends into the gas bubble 20. The ratio of the diameter of the round rod element 22 to the inner diameter of the circular sensor electrode housing 12 is ideally less than twenty.

Figure 2:
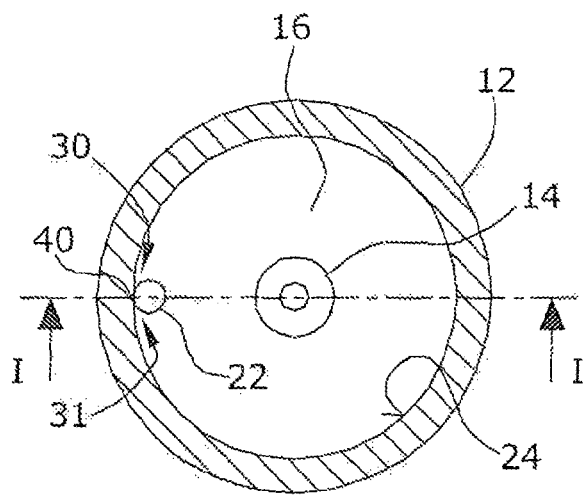
FIG. 2 shows a cross sectional view of the sensor electrode in FIG. 1.
Figure 3:
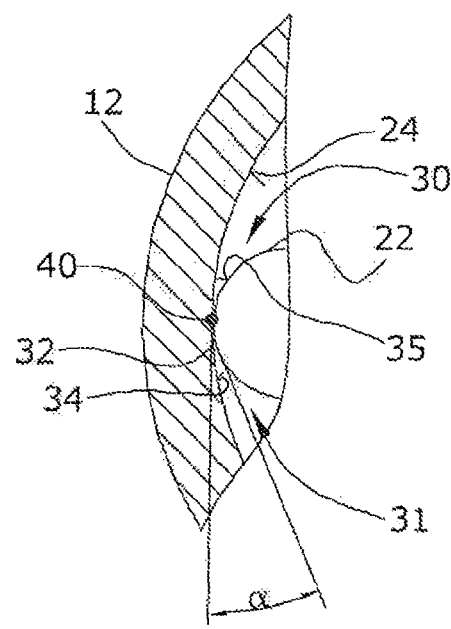
FIG. 3 shows an enlarged detail of the cross sectional view in FIG. 2.

FIG. 2 is a cross sectional view, while FIG. 3 is an enlarged detail of the cross sectional view of the water analysis sensor electrode 10 in FIG. 1. It can be seen that on either side of a contact line 40 between the rod element 22 and the inner wall 24, a respective tangentially open and substantially wedge-shaped capillary channel 30, 31 is formed. These capillary channels 30, 31 respectively extend along the full axial length of the rod element 22. The capillary channel wall 34 formed by the inner wall 24 and the capillary channel wall 35 formed by the rod element 22 include a wedge angle α, the wedge angle α being smaller than the contact angle of the sensor electrode housing material.

In an embodiment of the present invention, the rod element 22 may be formed integrally with the sensor electrode housing 12. Here, for reasons of manufacturing engineering, the wedge tip 32 cannot be formed perfectly pointed, but must have a rounded shape. The radius of the wedge tip 32 of the capillary channels 30, 31 should be at most 1.0 mm in such an embodiment.

The present invention is not limited to embodiments described herein; reference should be had to the appended claims.

The invention claimed is:

1. A water analysis sensor electrode for determining an analyte in water, the water analysis sensor electrode comprising:
 a sensor electrode housing which is configured to be closed, the sensor electrode housing comprising an inner wall and an ion-selective sensor electrode diaphragm arranged at a lower distal end of the sensor electrode housing;
 an electrolyte solution in the sensor electrode housing;
 a measuring electrode arranged in the sensor electrode housing;
 a gas bubble enclosed by the sensor electrode housing; and
 a rigid rod element having a round cross section arranged in the sensor electrode housing so that a continuous open capillary channel extends in a straight line over a length of the sensor electrode housing between the rigid rod element and the inner wall, the continuous open capillary channel being provided by the rigid rod element abutting against the inner wall of the sensor electrode housing via adhesion forces, the rigid rod element being made of glass, a metal, a ceramic or a plastic;
 wherein, the rigid rod element and the sensor electrode housing are not integral with each other.

2. The water analysis sensor electrode as recited in claim 1, wherein the rigid rod element is arranged to adhesively abut on the inner wall of the sensor electrode housing.

3. The water analysis sensor electrode as recited in claim 1, wherein a density of a material of the rigid rod element is higher than a density of the electrolyte solution.

4. The water analysis sensor electrode as recited in claim 1, wherein the sensor electrode housing is circular, and wherein a ratio of a diameter of the rigid rod element to a diameter of the sensor electrode housing is less than 20.

5. The water analysis sensor electrode as recited in claim 1, wherein an axial length of the rigid rod element is at least 3.0 mm larger than a level of the electrolyte solution in the sensor electrode housing.

6. The water analysis sensor electrode as recited in claim 5, wherein the axial length of the rigid rod element is at least 5.0 mm larger than the level of the electrolyte solution in the sensor electrode housing.

7. The water analysis sensor electrode as recited in claim 1, wherein an axial length of the rigid rod element is at least 3% longer than a level of the electrolyte solution in the sensor electrode housing.

8. The water analysis sensor electrode as recited in claim 7, wherein the axial length of the rigid rod element is at least 5% longer than the level of the electrolyte solution in the sensor electrode housing.

9. The water analysis sensor electrode as recited in claim 1, wherein an axial length of the rigid rod element is at least $7/10$ and at most $98/100$ of an axial inner length of the sensor electrode housing.

10. The water analysis sensor electrode as recited in claim 1, wherein the sensor electrode housing is circular, and wherein the sensor electrode housing has an inner diameter smaller than 15.0 mm.

11. The water analysis sensor electrode as recited in claim 1, wherein
    the rigid rod element is arranged in the sensor electrode housing so that the continuous open capillary channel extending over the length of the sensor electrode housing between the rigid rod element and the inner wall forms capillary channel walls have a wedge angle (a),
    a housing material, the electrolyte solution, and a gas in the gas bubble define a contact angle, and
    the wedge angle (a) is smaller than the contact angle.

\* \* \* \* \*